(12) United States Patent
Bühler et al.

(10) Patent No.: US 6,592,900 B1
(45) Date of Patent: Jul. 15, 2003

(54) STABILIZED POLYVINYLPYRROLIDONE FORMULATION

(75) Inventors: Volker Bühler, Wachenheim (DE); Ulrich Filges, Neustadt (DE); Tanja Schneider, Bensheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/701,871

(22) PCT Filed: Mar. 28, 2000

(86) PCT No.: PCT/EP00/02715

§ 371 (c)(1),
(2), (4) Date: Jan. 3, 2001

(87) PCT Pub. No.: WO00/59478

PCT Pub. Date: Oct. 12, 2000

(30) Foreign Application Priority Data

Apr. 6, 1999 (DE) .......................... 199 15 420

(51) Int. Cl.[7] .............................. A61K 9/14; A61K 9/00; A61K 9/50; A61K 33/34; A61K 33/30
(52) U.S. Cl. ..................... 424/489; 424/484; 424/486; 424/400; 424/501; 424/613; 424/614; 424/630
(58) Field of Search .................. 424/464, 489, 424/484, 486, 400, 501, 613, 614, 630, 639

(56) References Cited

U.S. PATENT DOCUMENTS

| 4,786,699 A | 11/1988 | Nuber et al. ............... 526/229 |
| 5,945,032 A | 8/1999 | Breitenbach et al. ....... 252/186 |

FOREIGN PATENT DOCUMENTS

| EP | 215 379 | | 3/1987 |
| EP | 832 846 | | 4/1998 |
| GB | 1 513 258 | * | 6/1978 |
| WO | WO 91/12825 | | 9/1991 |
| WO | WO 94/15648 | | 7/1994 |

OTHER PUBLICATIONS

Patel et al. "Povidone", Handbook of Pharmeaceutical Excipeints (1986) pp. 234–239.

* cited by examiner

Primary Examiner—Thurman K. Page
Assistant Examiner—Blessing Fubara
(74) Attorney, Agent, or Firm—Keil & Weinkauf

(57) ABSTRACT

Preparations in powder form comprising or consisting of soluble or insoluble polyvinylpyrrolidone and/or polyvinylpyrrolidone copolymers and suitable as aid for pharmaceutical formulations comprise in homogeneous dispersion very small amounts of heavy metals which are physiologically tolerated in these amounts, or very small amounts of peroxide-cleaving enzymes.

17 Claims, No Drawings

STABILIZED POLYVINYLPYRROLIDONE FORMULATION

This application is a 371 of PCT/EP00/02715 filed Mar. 28, 2000.

The invention relates to stabilized preparations in powder form comprising polyvinylpyrrolidone and/or polyvinylpyrrolidone copolymers and suitable as aid for pharmaceutical formulations, with an addition of very small amounts of heavy metals or peroxide-cleaving enzymes and to the production of these preparations.

Polymers such as homopolymeric, soluble or insoluble polyvinylpyrrolidone ("povidone" or "crospovidone") and the vinylpyrrolidone/vinyl acetate copolymer ("copovidone") are converted after their polymerization into a free-flowing powder by spray drying, drum drying or another hot air drying. During these processes, owing to the intensive contact with air and the heat, traces of peroxides are formed, and the content thereof increases during the subsequent packaging and storage. The maximum peroxide content in the substances is limited to 400 ppm in current Pharmacopeias, e.g. in Ph. Eur. 3 and JP XIII. Although drying with exclusion of air, storage at low temperatures or packaging hermetically sealed under vacuum or an inert gas are able to slow down the kinetics of peroxide formation, they cannot prevent it.

The various types of polyvinylpyrrolidone polymers mentioned (povidone, crospovidone and copovidone) are employed around the world as excipients in many different drug forms, with the use of binder and disintegrant in solid forms, e.g. for tablets and capsules, predominating. The excipients are likewise present in solid form in these medicaments and may, during the processing and storage together with sensitive active ingredients, have adverse effects on the stability thereof due to oxidation. Typical examples are ergot alkaloids, hormones, antibiotics such as doxycycline, metformin and molsidomine. There are for this reason narrow limits on the use of polyvinylpyrrolidone in combination with such oxidation-sensitive active ingredients. It is therefore easily possible in these cases to use only a freshly prepared polyvinylpyrrolidone whose peroxide content has not increased further due to storage. However, the provision of such a material often involves major problems of logistics in many countries around the world.

It is an object of the present invention to propose polyvinylpyrrolidone-containing aids with a greatly reduced peroxide content.

We have found that this object is achieved by preparations containing or consisting of soluble or insoluble polyvinylpyrrolidone and/or polyvinylpyrrolidone copolymers and suitable as aid for pharmaceutical formulations in powder form, which preparations comprise, in homogeneous dispersion, very small amounts of heavy metals which are physiologically tolerated in these amounts, or very small amounts of peroxide-cleaving enzymes.

It is true that the specialist literature discloses that polyvinylpyrrolidone also forms, in analogy to iodine, stoichiometric complexes with metals (e.g. with cobalt, nickel and manganese) and that these complexes catalyze the decomposition of hydrogen peroxide in aqueous solution at a pH above 7.3 (S. Sh. Rashidova, M. D. Inoyatov, Usb. Khim. Zh 3, pages 32–44, (1977)). It is equally known that hydrogen peroxide is specifically degraded by peroxidase or catalase in solution in the presence of polyvinylpyrrolidone (WO 9415648).

However, in all the cases described in the literature, high concentrations of the metal complexes and of the enzymes in solution are used.

It was now surprising that extremely small amounts, usually less than 10 ppm, of the heavy metals not only reduce the peroxide concentration in the solution but also have a stabilizing effect in the powder form, so that there is virtually no further increase in the peroxide content on storage, as occurred in the unstabilized preparation. This is astonishing since only a topochemical reaction is possible in the form in the solid state, and it was not to be expected with the great dilution of the stabilizer that any reaction at all is possible with the newly formed peroxides, which are likewise present in low concentration. Finally, the literature contains the information that polyvinylpyrrolidone is able not only to stabilize but also to inhibit enzymes, so that the regular advantageous effect of the enzymes added according to the invention was surprising also for this reason.

A relatively narrow range emerges for the addition of the heavy metals and/or enzymes. On the one hand, a particular amount is necessary for an effect. On the other hand, upper limits are set by reason of the physiological tolerability.

Addition of 10 ppm heavy metals (based on amount of metal by weight per amount of powdered aid by weight) will therefore usually not be exceeded. Amounts of from 1 to 10 ppm are preferred, in particular 5 to 8 ppm.

The upper limit for the enzymes is not critical for reasons of physiologically tolerability. Amounts of from 0.1 to 20, preferably 0.5 to 10, ppm are preferred.

Examples of suitable heavy metals are manganese, zinc, cobalt and, in particular, copper. Peroxide-cleaving enzymes used according to the invention are, in particular, catalase and peroxidase.

The procedure for producing the stabilized preparations is expedient such that the heavy metals are added in the form of their water-soluble salts, e.g. the sulfates or chlorides, to the solution or suspension of the polymers, and the solution or suspension is dried. Although the drying can be carried out in any suitable way, spray drying or drum drying is preferred.

Otherwise, these methods for producing the vinylpyrrolidone-containing aids are known, and reference is made to the standard literature for details.

The chemical and physical properties of the soluble (a) polyvinylpyrrolidones (povidone), insoluble (b) polyvinylpyrrolidone (crospovidone) and (c) polyvinylpyrrolidone copolymers, which are, for example, vinylpyrrolidone/vinyl acetate copolymers (copovidone), which are to be used according to the invention as aids, are also described in detail in the literature.

Polymers (a) are generally to be understood as those having an average molecular weight $M_W$ of from 2000 to 1,500,000 (=K value from 10 to 96) as are described in detail in the commentary in $9^{th}$ fascicule 1998 of the European Pharmacopoeia, Monograph "Povidonum". Reference is expressly made to this definition and the statements made therein are to be regarded as incorporated herein.

By (b) are meant popcorn polymers whose average molecular weight cannot be determined because they are entirely insoluble in all solvents. Since the IR spectrum is virtually identical to that of povidone (a), it can be assumed that they are substantially physically crosslinked homopolymers of vinylpyrrolidone like those described in the book "Kollidon, Polyvinylpyrrolidone for the pharmaceutical industry" $4^{th}$ edition 1999, BASF Aktiengesellschaft.

By (c) is meant soluble or partially insoluble copolymers of vinylimidazole, vinylcaprolactam with vinylpyrrolidone, $C_{1-18}$-alkyl esters of acrylic acid and methacrylic acid with vinylpyrrolidone, $C_{1-18}$-alkylvinyl esters of (meth)acrylic acid with vinylpyrrolidone. $C_{1-18}$-alkyl esters of acrylic acid or methacrylic acid mean, for example, ethyl acrylate, tert-butyl acrylate.

$C_{1-18}$-alkylvinyl esters can be, for example, vinyl acetate, vinyl propionate, stearyl (meth)acrylate, crotyl (meth)acrylate. Preferred copolymers are those of vinyl acetate and vinylpyrrolidone with a K value of from 20 to 50, whose solubility depends on the ratio of the two monomers. The ratio in this case is preferably 6 parts of vinylpyrrolidone to 4 parts of vinyl acetate, which affords a polymer which is still soluble in water and has a K value of 25 to 35, as likewise described in the book "Kollidon, Polyvinylpyrrolidone for the pharmaceutical industry" $4^{th}$ edition 1999, BASF Aktiengesellschaft.

The stabilization according to the invention is particularly suitable for those preparations intended to be used to produce tablets. The predominant use in this connection is that of povidone (a) and copovidone (c) as tablet binders with wet granules or as dry binders. For details, reference is made to the book "Kollidon, Polyvinylpyrrolidone for the pharmaceutical industry" $4^{th}$ edition 1999, BASF Aktiengesellschaft.

Another use is the provision of stabilized aids as disintegrants for tablets. Crospovidone (b) is particularly suitable for this.

Appropriate tablet formulations consist, for example, of active ingredient, bulking agent, povidone or copovidone as binder, crospovidone as sedimentation inhibitor, sucrose as bulking agent and flavoring, citric acid as ionic component, preservatives and water.

EXAMPLE 1

A solution of povidone K25 (polyvinylpyrrolidone; K value 25) was mixed with various amounts of a 0.01% strength copper chloride solution and dried at 100° C. The resulting powder was ground and stored in a closed vessel under an atmosphere of air at room temperature.

TABLE 1

| Amount of copper | Peroxide content after storage [ppm] | | | |
|---|---|---|---|---|
| added (based on the povidone powder) | After drying | After 6 months | After 12 months | After 24 months |
| 2 ppm | 58 | 253 | 276 | 322 |
| 4 ppm | 69 | 184 | 184 | 253 |
| 6 ppm | 69 | 69 | 69 | <50 |
| 8 ppm | 69 | 58 | <50 | <50 |

It is evident from Table 1 that there is only slight prevention of peroxide formation with addition of up to 4 ppm copper. After addition of 6 ppm copper, the peroxide content remains constant during storage, and with 8 ppm it in fact decreases during the storage period.

EXAMPLE 2

A solution of povidone K25 was mixed with various amounts of 0.01% strength solutions of copper chloride and cobalt chloride (1:1) and dried at 100° C. The resulting powder was ground and stored in a closed vessel under an atmosphere of air at room temperature.

TABLE 2

| Amount of metal | Peroxide content after storage [ppm] | | | |
|---|---|---|---|---|
| added (based on the povidone powder) | After drying | After 6 months | After 12 months | After 24 months |
| 1 ppm Cu + 1 ppm Co | 103 | 207 | 230 | 253 |
| 3 ppm Cu + 3 ppm Co | 69 | 184 | 270 | 276 |
| 4 ppm Cu + 4 ppm Co | 69 | 126 | 207 | 207 |
| 5 ppm Cu + 5 ppm Co | 69 | 69 | 58 | 69 |

Table 2 shows that copper alone has a greater effect.

EXAMPLE 3

A solution of povidone K30 was mixed with various amounts of a 0.01% strength copper chloride solution and spray dried, and the powder was stored in an open vessel at room temperature.

TABLE 3

| Amount of copper | Peroxide content after storage [ppm] | | | |
|---|---|---|---|---|
| added (based on the povidone powder) | After drying | After 1 month | After 2 months | After 6 months |
| 0 ppm | 69 | 139 | 161 | 230 |
| 4.7 ppm | 115 | 115 | 115 | 92 |
| 9.4 ppm | 69 | 46 | 46 | 23 |

EXAMPLE 4

A solution of a copolymer of 70% by weight vinylpyrrolidone and 30% by weight stearyl methacrylate was mixed with various amounts of a 0.01% strength copper chloride solution and dried at 100° C. The resulting product was stored in a closed vessel at room temperature under an air atmosphere.

TABLE 4

| Amounts of copper added (based on powder) [ppm] | Peroxide content after drying [ppm] | Peroxide content after storage for 4 weeks [ppm] |
|---|---|---|
| 0 | 30 | 62 |
| 7 | 30 | 24 |
| 10 | 30 | 22 |

It is evident from Table 4 that prevention of peroxide formation by adding copper is not confined to vinylpyrrolidone homopolymers, but also a comparable effect is shown on copolymers thereof.

EXAMPLE 5

The following example shows that even very small additions of the enzyme catalase react with and decompose the peroxides formed in the polyvinylpyrrolidone.

For this purpose, 50 g portions of an approximately 30% strength aqueous solution of two different batches of povidone K25 of different peroxide content (pH 3.0 to 5.0) were mixed with various amounts of 0.1 and 0.001% strength aqueous solutions of catalase and left to stand at room temperature for 1 hour, and the peroxide content therein was measured by the method in the Ph.Eur. "Povidone" monograph.

TABLE 5

| Amount of catalase added, calculated as powder | Peroxide content, based on the solution [ppm] | |
| --- | --- | --- |
|  | 1st povidone batch | 2nd povidone batch |
| no addition | 124 | 59 |
| 1 μg (0.07 ppm) | 122 | 57 |
| 10 μg (0.7 ppm) | 89 | 42 |
| 100 μg (6.7 ppm) | 26 | 26 |

We claim:

1. A method for stabilizing a preparation in powder form comprising a soluble or insoluble polyvinylpyrrolidone homo- or copolymer or a mixture thereof, and suitable as aid for pharmaceutical formulations, which comprises providing an aqueous solution of the homo- or copolymer or the mixture thereof, adding to the aqueous solution peroxide-cleaving enzymes in an amount of from 0.1 to 20 ppm, and optionally heavy metals in amounts which are physiologically tolerated, and converting the homo- or polymer or the mixture thereof into the powder form by drying.

2. The method of claim 1, wherein up to 10 ppm of heavy metals are added.

3. The method of claim 2, wherein a soluble copper salt is added as the heavy metal, and peroxidase or catalase is added as the peroxide-cleaving enzyme.

4. The method of claim 1, wherein the drying is carried out by spray drying or drum drying.

5. The method of claim 1, wherein the heavy metals are added in an amount of from 1 to 10 ppm.

6. The method of claim 5, wherein the heavy metals are selected from the group consisting of copper, cobalt, zinc and manganese.

7. The method of claim 1, wherein the heavy metals are selected from the group consisting of copper, cobalt, zinc and manganese.

8. The method of claim 1, wherein from 1 to 10 ppm copper are added.

9. The method of claim 1, wherein the peroxide-cleaving enzyme is catalase or peroxidase.

10. A method for stabilizing a preparation in powder form comprising a soluble or insoluble polyvinylpyrrolidone homo- or copolymer or a mixture thereof, and suitable as aid for pharmaceutical formulations, which comprises providing an aqueous solution of the homo- or copolymer or the mixture thereof, adding to the aqueous solution as a peroxide-cleaving enzyme catalase or peroxidase, and optionally heavy metals in amounts which are physiologically tolerated, and converting the homo- or polymer or the mixture thereof into the powder form by drying.

11. The method of claim 10, wherein up to 10 ppm of the heavy metals and up to 20 ppm of the enzyme are added.

12. The method of claim 11, wherein a soluble copper salt is added as the heavy metal.

13. The method of claim 10, wherein the drying is carried out by spray drying or drum drying.

14. The method of claim 11, wherein the heavy metals are added in an amount of from 1 to 10 ppm.

15. The method of claim 14, wherein the heavy metals are selected from the group consisting of copper, cobalt, zinc and manganese.

16. The method of claim 11, wherein the heavy metals are selected from the group consisting of copper, cobalt, zinc and manganese.

17. The method of claim 10, wherein from 1 to 10 ppm copper are added.

* * * * *